US011952293B2

(12) United States Patent
Wong et al.

(10) Patent No.: US 11,952,293 B2
(45) Date of Patent: Apr. 9, 2024

(54) APPARATUS FOR DISINFECTING A FLUID

(71) Applicant: International Water-Guard Industries Inc., Surrey (CA)

(72) Inventors: Jose Wong, Surrey (CA); Steven Bis, Surrey (CA)

(73) Assignee: International Water-Guard Industries Inc., Surrey (CA)

( * ) Notice: Subject to any disclaimer, the term of this patent is extended or adjusted under 35 U.S.C. 154(b) by 386 days.

(21) Appl. No.: 16/809,217

(22) Filed: Mar. 4, 2020

(65) Prior Publication Data
US 2020/0283311 A1 Sep. 10, 2020

Related U.S. Application Data

(60) Provisional application No. 62/815,029, filed on Mar. 7, 2019.

(51) Int. Cl.
*C02F 1/32* (2023.01)
*A61L 2/10* (2006.01)

(52) U.S. Cl.
CPC .................. *C02F 1/325* (2013.01); *A61L 2/10* (2013.01); *C02F 2201/3222* (2013.01); *C02F 2303/04* (2013.01)

(58) Field of Classification Search
CPC .............. C02F 1/325; C02F 2201/3222; C02F 2303/04; C02F 2201/3228; C02F 2201/328; C02F 2201/006; C02F 2201/3227; C02F 2201/008; C02F 1/001; C02F 2209/005; C02F 2209/001; C02F 2209/11; C02F 2209/40; C02F 2209/05; A61L 2/10; G01N 21/33; G01N 21/85; G01N 21/94
See application file for complete search history.

(56) References Cited

U.S. PATENT DOCUMENTS

| 6,707,048 B2 | 3/2004 | Hallett |
| 6,773,584 B2 | 8/2004 | Saccomanno |
| 7,169,311 B2 | 1/2007 | Saccomanno |

(Continued)

FOREIGN PATENT DOCUMENTS

| CA | 2747200 B2 | 6/2010 |
| CA | 3011888 A1 | 7/2017 |

(Continued)

OTHER PUBLICATIONS http://www.maximintegrated.com/an4481, Fons Janssen, "Soft-Start Enhances LED Driver," Maxim Integrated, Application Note 4481, 3 pages, Aug. 17, 2020.

*Primary Examiner* — Xiuyu Tai
(74) *Attorney, Agent, or Firm* — Klarquist Sparkman, LLP

(57) ABSTRACT

There is described an apparatus for disinfecting a fluid, such as water. The apparatus includes a housing having a fluid inlet for inflow of a fluid to be disinfected, and a fluid outlet for outflow of the fluid to be disinfected. The apparatus further includes one or more light-emitting diodes (LEDs) operable to emit ultraviolet (UV) light for disinfecting the fluid to be disinfected. A fluid flow path extends from the fluid inlet to the fluid outlet. The fluid flow path is configured such that, when the fluid to be disinfected flows along the fluid flow path, the fluid to be disinfected flows sufficiently close to the one or more LEDs so as to absorb heat generated by the one or more LEDs.

28 Claims, 8 Drawing Sheets

(56) References Cited

U.S. PATENT DOCUMENTS

| | | |
|---|---|---|
| 7,534,356 B2 | 5/2009 | Saccomanno |
| 7,819,556 B2 | 10/2010 | Heffington |
| 8,674,322 B2 | 3/2014 | Kohler |
| 8,742,364 B2 | 6/2014 | Boodaghians |
| 9,260,323 B2 | 2/2016 | Boodaghians |
| 9,381,458 B2 | 7/2016 | Blechschmidt |
| 9,409,797 B2 | 8/2016 | Wipprich |
| 9,475,708 B2 | 10/2016 | Rajagopalan |
| 9,540,252 B1 | 1/2017 | Collins |
| 9,566,358 B1 | 2/2017 | Koh |
| 9,617,171 B2 | 4/2017 | Rajagopalan |
| 9,695,062 B2 | 7/2017 | Rajagopalan |
| 9,718,706 B2 | 8/2017 | Smetona |
| 9,738,547 B2 | 8/2017 | Schmitt |
| 9,834,456 B2 | 12/2017 | Collins |
| 10,040,699 B2 | 8/2018 | Smetona |
| 10,077,194 B2 | 9/2018 | Knight |
| 10,093,558 B2 | 10/2018 | Smetona |
| 10,099,944 B2 | 10/2018 | Smetona |
| 10,658,549 B2 | 5/2020 | Ahn et al. |
| 2007/0163934 A1* | 7/2007 | Kim ............... C02F 1/325 250/436 |
| 2008/0095661 A1 | 4/2008 | Kohler |
| 2010/0044319 A1* | 2/2010 | Engel ............... A61L 9/20 210/85 |
| 2011/0150707 A1* | 6/2011 | Kobayashi ......... C02F 1/325 422/186.3 |
| 2015/0114912 A1 | 4/2015 | Taghipour |
| 2015/0144575 A1 | 5/2015 | Hawkins, II |
| 2015/0314024 A1 | 11/2015 | Khan |
| 2016/0083272 A1 | 3/2016 | Rajagopalan |
| 2016/0331855 A1 | 11/2016 | St. Louis |
| 2018/0334400 A1 | 11/2018 | Gummer |
| 2019/0165219 A1 | 5/2019 | Ahn et al. |
| 2019/0225509 A1* | 7/2019 | Dhiman .............. C02F 1/325 |
| 2020/0009279 A1* | 1/2020 | Janssen ............... A61L 9/20 |

FOREIGN PATENT DOCUMENTS

| | | |
|---|---|---|
| CA | 3011890 A1 | 7/2017 |
| CA | 2965282 A1 | 10/2018 |
| DE | 202011000503 B1 | 12/2011 |
| DE | 102013103517 A1 | 10/2014 |
| DE | 112015005371 A1 | 10/2017 |
| DE | 102014015642 B2 | 6/2018 |
| DE | 102017116155 B2 | 10/2018 |
| DE | 102017117324 A1 | 1/2019 |
| EP | 2567713 B1 | 10/2014 |
| EP | 2999667 B1 | 2/2017 |
| EP | 2999669 B1 | 2/2017 |
| EP | 3388087 A1 | 10/2018 |
| EP | 3170796 B1 | 2/2019 |
| GB | 2525360 B1 | 3/2016 |
| KR | 2019-0096020 A | 8/2019 |
| WO | 2014122185 A1 | 8/2014 |
| WO | 2016085385 A1 | 6/2016 |
| WO | 2016150718 A1 | 9/2016 |
| WO | 2017099033 A1 | 6/2017 |
| WO | 2017115394 A1 | 7/2017 |
| WO | 2017124190 A1 | 7/2017 |
| WO | 2017124191 A1 | 7/2017 |
| WO | 2018048654 A1 | 3/2018 |
| WO | 2018213936 A1 | 11/2018 |
| WO | 2019013539 A1 | 1/2019 |
| WO | WO2020/009294 A1 | 1/2020 |
| WO | WO2020/022590 A1 | 1/2020 |

* cited by examiner

→ Water used for Cooling
⇒ Disinfected Water

APPARATUS FOR DISINFECTING A FLUID

CROSS REFERENCE TO RELATED APPLICATION

This application claims the benefit of U.S. Provisional Patent Application No. 62/815,029, filed Mar. 7, 2019, which is incorporated herein by reference.

FIELD OF THE DISCLOSURE

The present disclosure relates to an apparatus for disinfecting a fluid such as water.

BACKGROUND OF THE DISCLOSURE

Drinking water typically requires disinfection before it can be delivered to users. For example, in the aviation industry, water stored onboard an aircraft may be disinfected prior to delivery to the crew and passengers. For example, the stored water may be pumped through a disinfection reactor before being delivered to one or more faucets. As the water flows through the reactor, it is exposed to ultraviolet (UV) light from one or more UV-light sources, and is therefore disinfected.

Prior art disinfection reactors have generally relied on mercury lamps to disinfect water. More recently, light-emitting diodes (LEDs) have come to replace such lamps, in part due to their lower cost and increased energy efficiency. LEDs, however, typically generate substantial amounts of heat during operation, and require cooling in order to be operated for extended periods of time. Insufficient cooling may risk the LEDs overheating, whereas operating the LEDs at a lower power to mitigate the risk of overheating may result in inadequate disinfection.

The present disclosure relates to improvements in a UV-LED-based disinfection apparatus.

SUMMARY OF THE DISCLOSURE

According to a first aspect of the disclosure, there is provided an apparatus for disinfecting a fluid, comprising: a housing comprising: a fluid inlet for inflow of a fluid to be disinfected; and a fluid outlet for outflow of the fluid to be disinfected; and one or more light-emitting diodes (LEDs) operable to emit ultraviolet (UV) light for disinfecting the fluid to be disinfected, wherein fluid flow path extends from the fluid inlet to the fluid outlet and is configured such that, when the fluid to be disinfected flows along the fluid flow path, the fluid to be disinfected flows sufficiently close to the one or more LEDs so as to absorb heat generated by the one or more LEDs.

The one or more LEDs may be mounted on one or more substrates, and the one or more substrates may define a boundary of at least a portion of the fluid flow path such that, when the fluid to be disinfected flows along the fluid flow path, the fluid to be disinfected flows in contact with the one or more substrates. The one or more substrates may comprise one or more printed circuit boards (PCBs).

The one or more LEDs may be mounted on one or more substrates, the apparatus may further comprise a conductive member on which are provided the one or more substrates, and the conductive member may define a boundary of at least a portion of the fluid flow path such that, when the fluid to be disinfected flows along the fluid flow path, the fluid to be disinfected flows in contact with the conductive member.

A distance between the one or more portions of the fluid flow path and the one or more LEDs may be configured such that, when the fluid to be disinfected flows along the fluid flow path, at least about 90% of heat generated by the one or more LEDs is absorbed by the fluid to be disinfected.

One or more of the following may be selected such that, when the fluid to be disinfected flows along the fluid flow path, the fluid to be disinfected is disinfected at a rate of at least about 16 mJ/cm$^2$ at 90% UV transmissivity of the fluid: a length of the fluid flow path; a setting of a flow regulator for controlling a rate of flow of the fluid to be disinfected; and a power output of the one or more LEDs.

The apparatus may further comprise one or more baffles defining one or more portions of the fluid flow path such that the fluid flow path comprises one or more first branches extending in a first direction, and one or more second branches extending in a second direction opposite the first direction. The one or more baffles may further define one or more annular spaces within the housing. The one or more annular spaces may be concentric.

The one or more baffles may be configured such that, when the fluid to be disinfected flows along the fluid flow path, the fluid to be disinfected flows from a near end to an opposite far end of a first one of the one or more annular spaces, and then from a far end to an opposite near end of a second one of the one or more annular spaces.

The one or more annular spaces may comprise a sequence of annular spaces, and the one or more baffles may be configured such that, when the fluid to be disinfected flows along the fluid flow path, the fluid to be disinfected flows sequentially from one annular space to the next annular space in the sequence of annular spaces.

The one or more baffles may be configured such that a direction of the fluid flow path is reversed at least once.

The one or more baffles may comprise one or more portions that are at least partially transparent to UV light.

The one or more LEDs may define one or more light beams, and: one or more first portions of the fluid flow path may not pass through the one or more light beams; and/or one or more second portions of the fluid flow path may pass through the one or more light beams.

One or more first portions of the fluid flow path may pass behind the one or more LEDs such that, when the fluid to be disinfected flows along the one or more first portions of the fluid flow path, the fluid to be disinfected flows sufficiently close to the one or more LEDs so as to absorb, from behind the one or more LEDs, heat generated by the one or more LEDs.

One or more second portions of the fluid flow path may pass in front of the one or more LEDs such that, when the fluid to be disinfected flows along the one or more second portions of the fluid flow path, the fluid to be disinfected flows sufficiently close to the one or more LEDs so as to absorb, from in front of the one or more LEDs, heat generated by the one or more LEDs.

The fluid flow path may be further configured such that, when the fluid to be disinfected flows along the fluid flow path, the fluid to be disinfected flows sequentially from the fluid inlet, to the one or more first portions of the fluid flow path, to one or more second portions of the fluid flow path, and to the fluid outlet. The fluid flow path may be further configured such that, when the fluid to be disinfected flows along the fluid flow path, the fluid to be disinfected flows further via the one or more annular spaces when flowing from the one or more first portions of the fluid flow path to the one or more second portions of the fluid flow path.

The apparatus may further comprise: a window at least partially transparent to UV light, positioned in front of the one or more LEDs; and a conductive material positioned between the one or more LEDs and the window. The conductive material may comprise a thermally conductive foam. The conductive material may be in contact with the one or more LEDs and the window.

The window may define a boundary of at least a portion of the fluid flow path such that, when the fluid to be disinfected flows along the fluid flow path, the fluid to be disinfected flows in contact with the window.

The fluid inlet may be off-axis relative to the one or more LEDs.

The housing may comprise a reflective surface for reflecting UV light. For example, the housing may be formed of a material reflective to UV light.

The apparatus may further comprise a controller configured to control the one or more LEDs. The controller may be further configured to gradually increase and/or decrease a current drawn by at least one of the one or more LEDs.

The one or more LEDs may comprise multiple LEDs, and the controller may be further configured to sequentially activate and/or deactivate the LEDs.

The controller may be further configured to activate an alarm in response to determining that a disinfection rate, or a UV transmissivity of the fluid, has dropped below a preset threshold. The controller may be further configured to determine whether the disinfection rate, or the UV transmissivity, has dropped below the preset threshold based on one or more of: a flow rate of the fluid to be disinfected; an intensity of UV light reflected from the housing; a duration that the one or more LEDs have been operated for; and a power output of the one or more LEDs.

The controller may comprise: circuitry; or one or more processors communicative with memory having stored thereon computer program code executable by the one or more processors.

The controller may be further configured to: determine an intensity of UV light having passed through a fluid flowing through the apparatus; determine whether the measured intensity is outside a threshold window; and if the measured intensity is outside the threshold window, adjust a current driving the one or more LEDs.

The one or more LEDs may comprise multiple groups of LEDs, each group of LEDs may comprise one or more LEDs, and the controller may be further configured to, after determining that the measured intensity is outside the threshold window and before adjusting the current: sequentially drive each group of LEDs; and for each group of LEDs, determine whether a power output of at least one of the LEDs in the group of LEDs is less than an expected power output; and if the power output of the at least one of the LEDs is less than the expected power output, then the adjusting of the current driving the one or more LEDs is based on the power output of the at least one of the LEDs, to compensate for the power output of the at least one of the LEDs; and if the power output of the at least one of the LEDs is not less than the expected power output, then the controller is further configured to adjust a UV transmissivity value of the fluid, and wherein the adjusting of the current driving the one or more LEDs is based on the adjusted UV transmissivity value, to compensate for the adjusted UV transmissivity value.

Determining whether the power output of the at least one of the LEDs is less than an expected power output may comprise: determining with the controller an intensity of UV light having passed through a fluid flowing through the apparatus; and determining with the controller whether the measured intensity of UV light is below an expected threshold.

If compensating for the adjusted UV transmissivity value or the power output of the at least one of the LEDs would require the current driving the one or more LEDs to be increased beyond a maximum driving current, then the controller may be further configured to activate an alarm.

The apparatus may further comprise one or more sensors for detecting an intensity of UV light that has passed through a fluid flowing through the apparatus, and/or that has been reflected from the housing.

The apparatus may further comprise a flow regulator for controlling a flow of the fluid to be disinfected through the apparatus.

The apparatus may further comprise a flow sensor for detecting a flow rate of the fluid to be disinfected through the apparatus.

The apparatus may not comprise any additional means for cooling the one or more LEDs. The additional means may comprise a separate fluid inlet and a separate fluid outlet for receiving a separate coolant for cooling the one or more LEDs. The additional means may comprise a heatsink.

The apparatus may further comprise one or more baffles defining one or more portions of the fluid flow path, and each baffle may comprise one or more apertures formed therein. The one or more baffles may comprise a sequence of baffles comprising a sequence of one or more disc-shaped baffles and one or more annulus-shaped baffles, each disc-shaped baffle may comprise one more peripherally-located apertures, and each annulus-shaped baffle may comprise a centrally-located aperture. In the sequence of baffles, the one or more disc-shaped baffles may alternate with the one or more annulus-shaped baffles.

In a further aspect of the disclosure, there is provided a method of disinfecting a fluid, comprising: providing an apparatus comprising: a housing comprising: a fluid inlet; and a fluid outlet; and one or more light-emitting diodes (LEDs) operable to emit ultraviolet (UV) light, wherein a fluid flow path extends from the fluid inlet to the fluid outlet and is configured such that, when a fluid flows along the fluid flow path, the fluid flows sufficiently close to the one or more LEDs so as to absorb heat generated by the one or more LEDs; flowing a fluid from the fluid inlet to the fluid outlet, via the fluid flow path; and operating the one or more LEDs.

In a further aspect of the disclosure, there is provided a method of operating one or more light-emitting diodes (LEDs) in a fluid disinfection apparatus, the one or more LEDs being operable to emit ultraviolet (UV) light, the method comprising: measuring an intensity of UV light having passed through a fluid flowing through the apparatus; determining whether the measured intensity is outside a threshold window; and if the measured intensity is outside the threshold window, adjusting a current driving the one or more LEDs.

The one or more LEDs may comprise multiple groups of LEDs, each group of LEDs may comprise one or more LEDs, and the method may further comprise, after determining that the measured intensity is outside the threshold window and before adjusting the current: sequentially driving each group of LEDs; and for each group of LEDs, determining whether a power output of at least one of the LEDs in the group of LEDs is less than an expected power output; and if the power output of the at least one of the LEDs is less than the expected power output, then the adjusting of the current driving the one or more LEDs is based on the power output of the at least one of the LEDs, to compensate for the power output of the at least one of the LEDs; and if the power output of the at least one of the LEDs is not less than the expected power output, then adjusting a UV transmissivity value of the fluid, and wherein the adjusting of the current driving the one or more LEDs is based on the adjusted UV transmissivity value, to compensate for the adjusted UV transmissivity value.

Determining whether the power output of the at least one of the LEDs is less than an expected power output may comprise: measuring an intensity of UV light having passed through a fluid flowing through the apparatus; and determining whether the measured intensity of UV light is below an expected threshold.

If compensating for the adjusted UV transmissivity value or the power output of the at least one of the LEDs would require the current driving the one or more LEDs to be increased beyond a maximum driving current, then the method may further comprise activating an alarm.

Throughout the disclosure, the term fluid inlet encompasses more than one fluid inlet, and the term fluid outlet encompasses more than one fluid outlet.

BRIEF DESCRIPTION OF THE DRAWINGS

Embodiments of the disclosure will now be described in detail in conjunction with the accompanying drawings of which.

DETAILED DESCRIPTION OF SPECIFIC EMBODIMENTS

Figure 1:
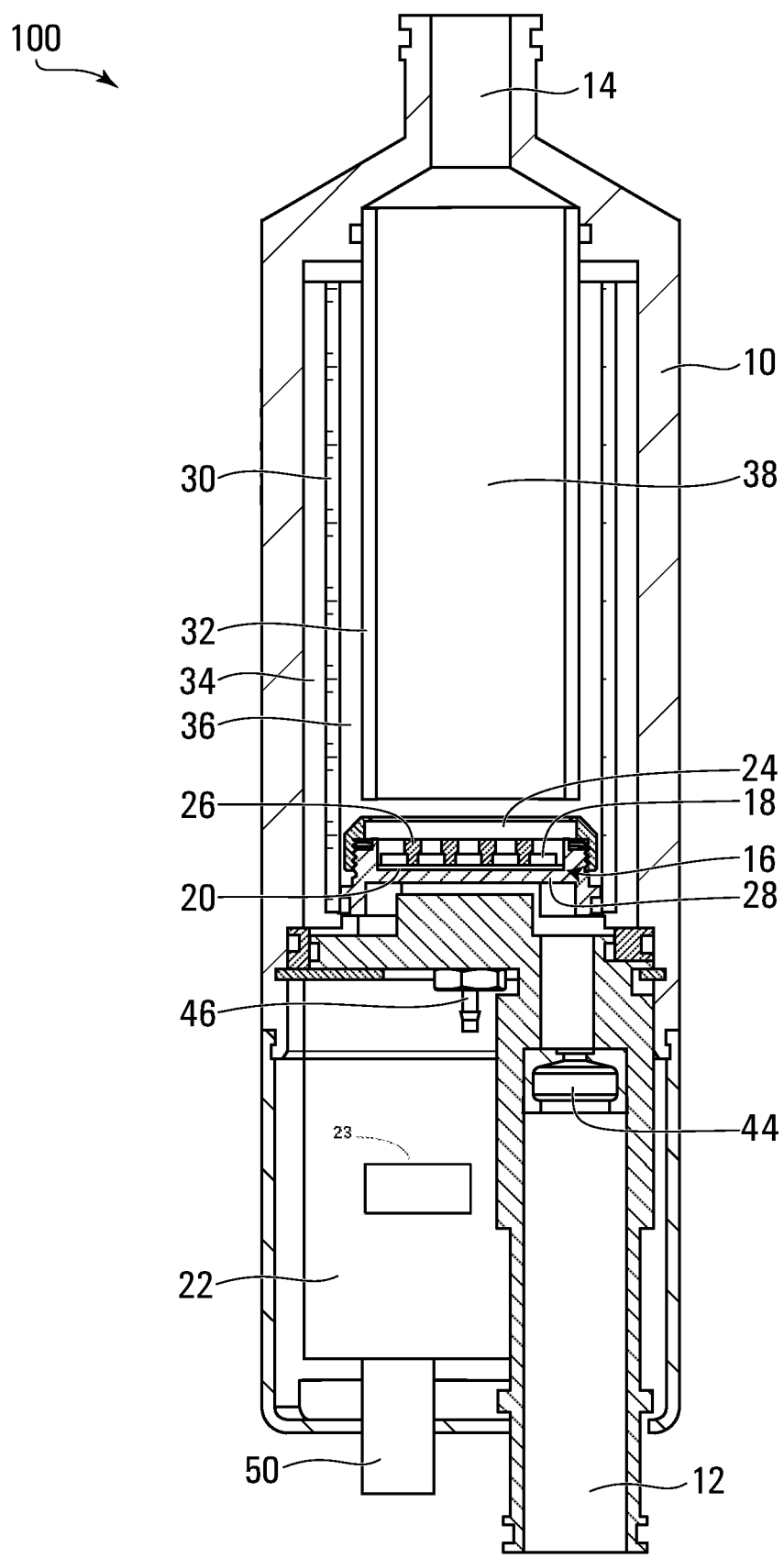
FIG. 1 is a first cross-sectional view of an apparatus for disinfecting a fluid, according to embodiments of the disclosure.

The present disclosure seeks to provide an improved apparatus for disinfecting a fluid. While various embodiments of the disclosure are described below, the disclosure is not limited to these embodiments, and variations of these embodiments may well fall within the scope of the disclosure which is to be limited only by the appended claims.

The word "a" or "an" when used in conjunction with the term "comprising" or "including" in the claims and/or the specification may mean "one", but it is also consistent with the meaning of "one or more", "at least one", and "one or more than one" unless the content clearly dictates otherwise. Similarly, the word "another" may mean at least a second or more unless the content clearly dictates otherwise.

The terms "coupled", "coupling" or "connected" as used herein can have several different meanings depending on the context in which these terms are used. For example, the terms coupled, coupling, or connected can have a mechanical or electrical connotation. For example, as used herein, the terms coupled, coupling, or connected can indicate that two elements or devices are directly connected to one another or connected to one another through one or more intermediate elements or devices via an electrical element, electrical signal or a mechanical element depending on the particular context. The term "and/or" herein when used in association with a list of items means any one or more of the items comprising that list.

As used herein, a reference to "about" or "approximately" a number or to being "substantially" equal to a number means being within +/−10% of that number.

Generally, according to embodiments of the disclosure, there is described an apparatus for disinfecting a fluid. The apparatus is designed to permit a fluid that is to be disinfected, such as water that is to be used for drinking, to flow into a housing via one or more fluid inlets ("the fluid inlet"). Within the housing, the fluid flows along a fluid flow path from the fluid inlet to one or more fluid outlets ("the fluid outlet"), whereupon the fluid exits the apparatus. Within the housing are provided one or more LEDs operable to emit light having one or more wavelengths in the UV range. For example, according to some embodiments, the one or more LEDs may be operable to emit light with a wavelength in the range of 260 nm-275 nm. The LEDs and the fluid flow path are configured such that the emitted UV light intersects the fluid flow path at one or more points. Thus, as the fluid flows through the apparatus, it is subjected to the UV light and as a result undergoes disinfection.

Depending on the current that is being drawn, LEDs can generate substantial amounts of heat during operation, and therefore often require some form of cooling. In order to cool the LEDs during operation, the fluid flow path is configured so as to bring the fluid within relatively close proximity of the LEDs. In particular, the LEDs may be mounted on one or more printed circuit boards (PCBs) which may be disposed or otherwise in contact with a conductive plate. The conductive plate may define a portion of a boundary of the fluid flow path, such that the fluid is brought into contact with the conductive plate as the fluid flows along the fluid flow path. By coming into contact with the conductive plate, the fluid draws heat away from the LEDs (and away from the PCB on which are mounted the LEDs). In addition, the fluid flow path may be further configured such that the fluid is brought into contact with a window positioned in front of the LEDs. The window may itself be in contact with a conductive material which in turn may be in contact with the LEDs. Thus, heat may be drawn away from the LEDs by fluid flow both from behind and in front of the LEDs. Advantageously, the fluid to be disinfected acts as a coolant. There therefore may be no need for any additional cooling means.

In order to facilitate effective disinfection of the fluid, the fluid flow path may be deliberately extended within the housing, through the use of one or more UV-transparent baffles. For example, the direction of the fluid flow path may be reversed or altered by the baffles one or more times such that the fluid flow path is sinusoidally, circuitously, or otherwise tortuously disposed within the housing. In this manner, the fluid is exposed to the UV light for a greater period of time than if the fluid flow path simply took a more direct route from the fluid inlet to the fluid outlet.

Embodiments of the disclosure will now be described in more detail.

Turning to FIG. 1, there is shown a cross-sectional view of an apparatus 100 for disinfecting a fluid. Apparatus 100 comprises a generally cylindrical structure or housing 10 having a fluid inlet 12 at one end thereof and a fluid outlet 14 at an opposite end thereof. Housing 10 is formed of or otherwise comprises a UV-reflective material such as Teflon.

Apparatus 100 further includes an LED module 16 housing an LED array comprising multiple groups of one or more LEDs 18. Each LED 18 is configured to emit UV light in the range of 260 nm-275 nm, although according to some embodiments other suitable UV wavelengths may be used. LEDs 18 are mounted on a first PCB 20 and are operably connected to a controller 23 provided on a second PCB 22. The controller 23 is configured to drive LEDs 18 according to one or more various control methods or algorithms, as described in further detail below.

LED module 16 comprises an optical window 24 provided in front of LEDs 18. According to the present embodiment, optical window 24 comprises quartz, but other suitable materials may be used. Further housed within LED module 16 is a conductive material 26 provided between optical window 24 and LEDs 18. Conductive material 26 comprises a foam containing a conductive paste. Conductive material 26 extends from LEDs 18 to optical window 24, and acts to conductively couple LEDs 18 and optical window 24, thereby facilitating the transfer of heat from LEDs 18 to optical window 24.

Figure 2:
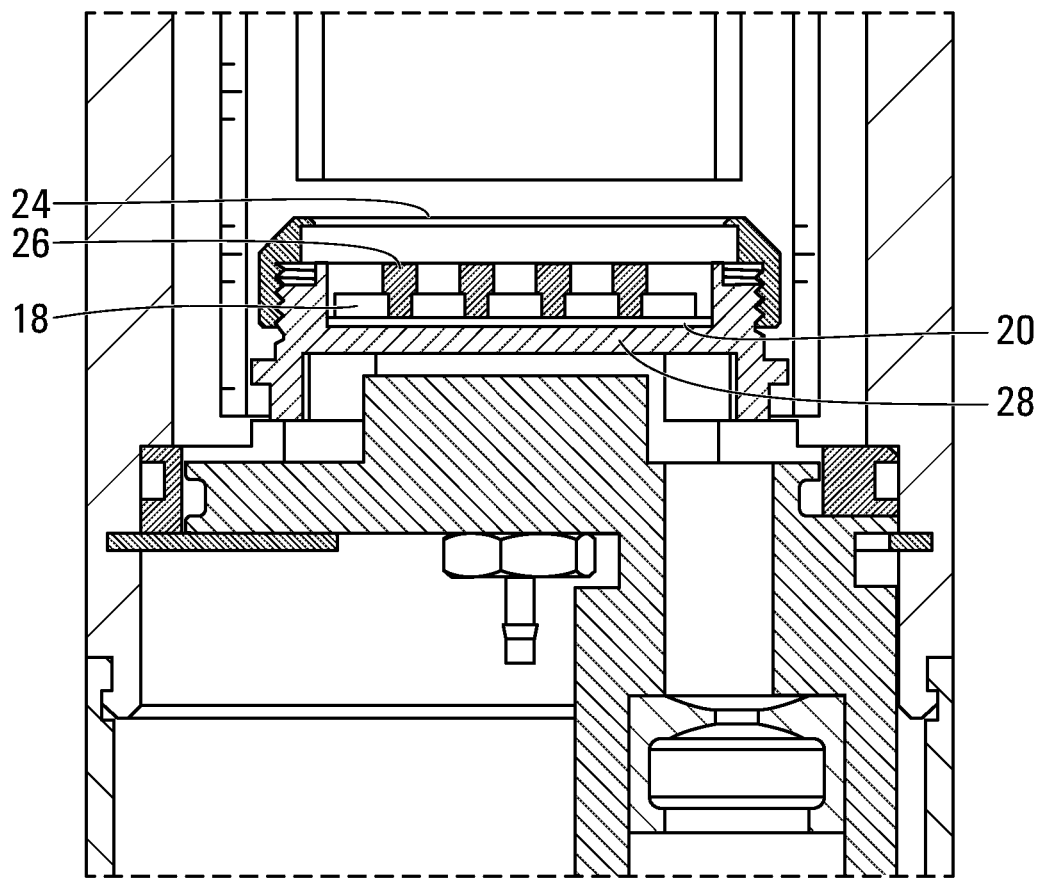
FIG. 2 shows a magnified portion of the apparatus of FIG. 1.

A rear of LED module 16 is provided with a conductive member 28 against which is positioned PCB 20. Conductive member 28 may be, for example, a stainless steel plate. Conductive member 28 and optical window 24 serve to fluidly seal LED module 16. LED module 16 and its components are shown in more detail in FIG. 2.

Apparatus 100 further includes multiple cylindrical baffles, and in particular a first cylindrical baffle 30 and a second cylindrical baffle 32. Baffles 30 and 32 define first and second concentric annular spaces 34 and 36. Annular spaces 34 and 36 are disposed about a central, cylindrical chamber 38 defined by cylindrical baffle 32. Chamber 38 is fluidly coupled to fluid outlet 14. Baffles 30 and 32 are formed of a material, such as quartz, that is largely optically transparent to UV light.

Apparatus 100 further includes a flow regulator 44 for controlling a rate of flow of a fluid flowing into apparatus 100 via fluid inlet 12, and a flow detection port 46 for detecting or sensing a rate of flow of a fluid flowing through apparatus 100. For example, flow regulator 44 may limit a maximum flow rate of fluid through apparatus 100 to 1 gallon/minute. Apparatus 100 further includes a power and communications connector 50 for coupling PCB 22 to an external power source.

Baffles 30 and 32, in combination with portions of housing 10, define a fluid flow path extending from fluid inlet 12 to fluid outlet 14. The fluid flow path is shown in more detail in FIG. 3. As can be seen from FIG. 3, the fluid flow path extends from fluid inlet 12 to a first, rear chamber 40 located at the rear of LED module 16, adjacent conductive member 28. Fluid flowing into apparatus 100 via fluid inlet 12 therefore flows into rear chamber 40. After entering rear chamber 40, the fluid is directed via one or more apertures formed within rear chamber 40 to first annular space 34. The fluid flow path then extends from a near end of annular space 34 to a far end of annular space 34. In the context of the present embodiment, a near end may be an end closest to LED module 16, and a far end may be an end furthest from LED module 16.

At the far end of annular space 34, the fluid flow path extends into adjacently disposed second annular space 36. The fluid flow path then extends from a far end of annular space 36 to a near end of annular space 36, whereupon the fluid flow path passes into a second, front chamber 42 located in front of LED module 16. Thus, fluid flowing out of rear chamber 40 flows into and along annular space 34, then into and along annular space 36, and then into front chamber 42. The fluid flow path then passes into chamber 38 via one or more apertures formed within front chamber 42, and finally out of apparatus 100 via fluid outlet 14. Thus, baffles 30 and 32 serve to reverse multiple times a direction of the fluid flow path.

Figure 3:
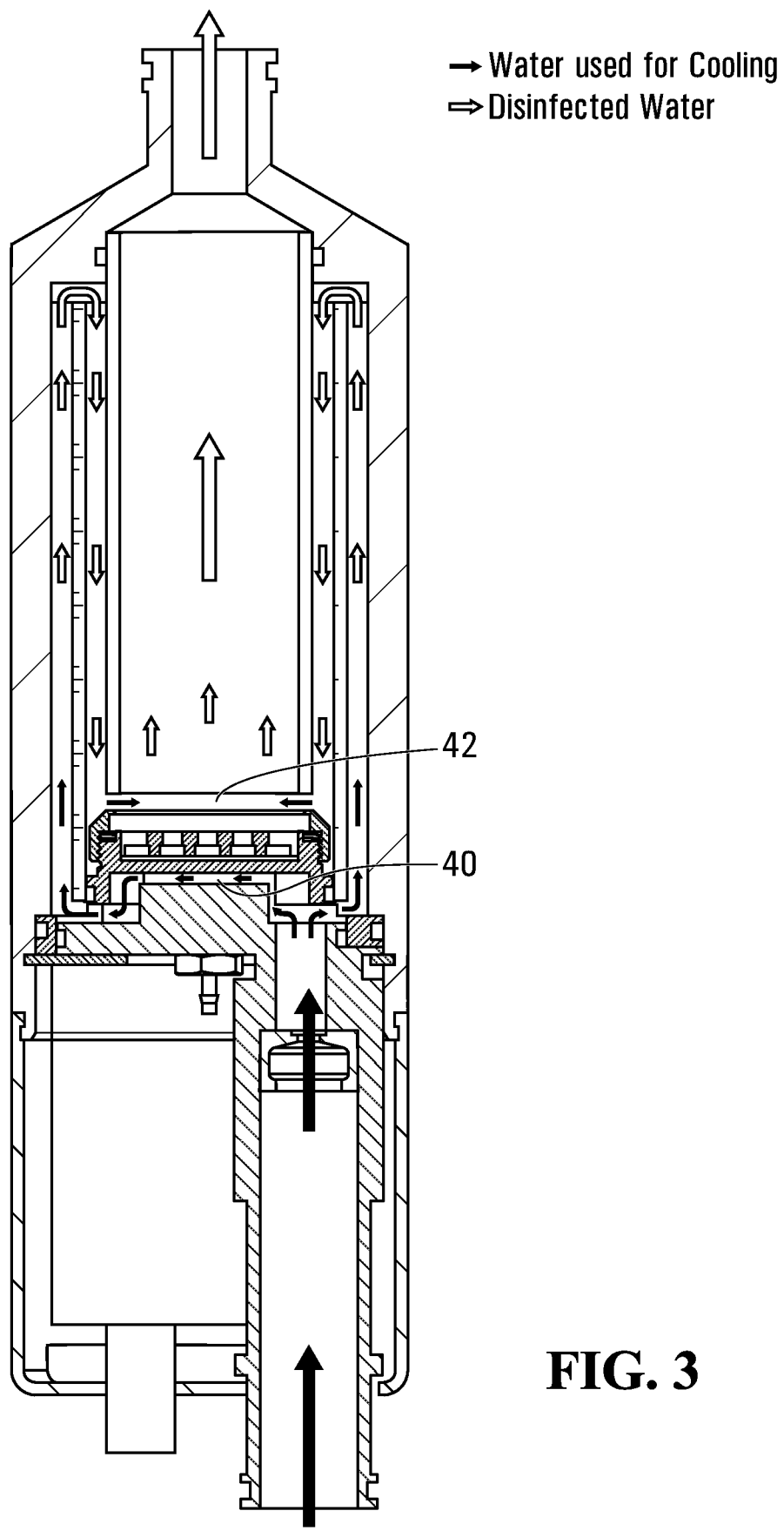
FIG. 3 is a second cross-sectional view of the apparatus of FIG. 1.

As can be seen from the above description and FIG. 3, the fluid flow path is configured such that, when the fluid to be disinfected flows along the fluid flow path, the fluid to be disinfected flows adjacent LED module 16 on two separate occasions. In particular, the fluid is brought sufficiently close to LEDs 18 and PCB 20 so as to absorb heat generated by LEDs 18 during their operation. According to some embodiments, a distance of about 1.5 mm separates PCB 20 from rear chamber 40.

By virtue of the fluid flowing within rear chamber 40, the fluid flows into contact with conductive member 28 and draws heat generated by LEDs 18 through a rear of LED module 16, via PCB 20 and conductive member 28. Furthermore, by virtue of the fluid flowing within front chamber 42, the fluid flows into contact with optical window 24 and draws heat generated by LEDs 18 through a front of LED module 16, via conductive material 26 and optical window 24. While optical window 24 may not be particularly conductive, conductive material 26 assists in transferring heat generated by LEDs 18 to the fluid.

During operation of LEDs 18, the fluid is subjected to disinfection by UV light emitted from LEDs 18. Furthermore, by virtue of baffles 30 and 32, a duration during which the fluid flowing through apparatus 100 is subjected to UV light may be increased when compared to when the fluid flow path takes a more direct route from fluid inlet 12 to fluid outlet 14. Baffles 30 and 32 are substantially transparent to UV light, and therefore the fluid undergoes disinfection as it flows along annular spaces 34 and 36.

In FIG. 3, portions of the fluid flow path that pass through rear and front chambers 40 and 42 (and therefore are associated with cooling) are shown in blue arrows, and portions of the fluid flow path that pass through first and second annular spaces 34 and 36, and through chamber 38 (and therefore are associated with disinfection), are shown in green arrows. Fluid flowing in contact with optical window 28 provides both a cooling function as well as simultaneously undergoing disinfection.

According to embodiments described herein, a majority, such as about 90% or more, of heat generated by LEDs 18 may be absorbed by the fluid flowing through apparatus 100. To adjust the cooling effect of the fluid on LEDs 18, various parameters of apparatus 100 may be varied. For example, the total length of the fluid flow path may be adjusted, as well as the power output by LEDs 18, the rate of flow of the fluid through apparatus 100, and a temperature of the fluid entering apparatus 100.

As mentioned above, LEDs 18 are controlled by a controller provided on PCB 22. The controller may comprise circuitry configured to perform any of the methods described below, and/or may comprise a microprocessor or similar device that is communicative with memory on which are stored the instructions for performing any of the methods described below.

Figure 4:
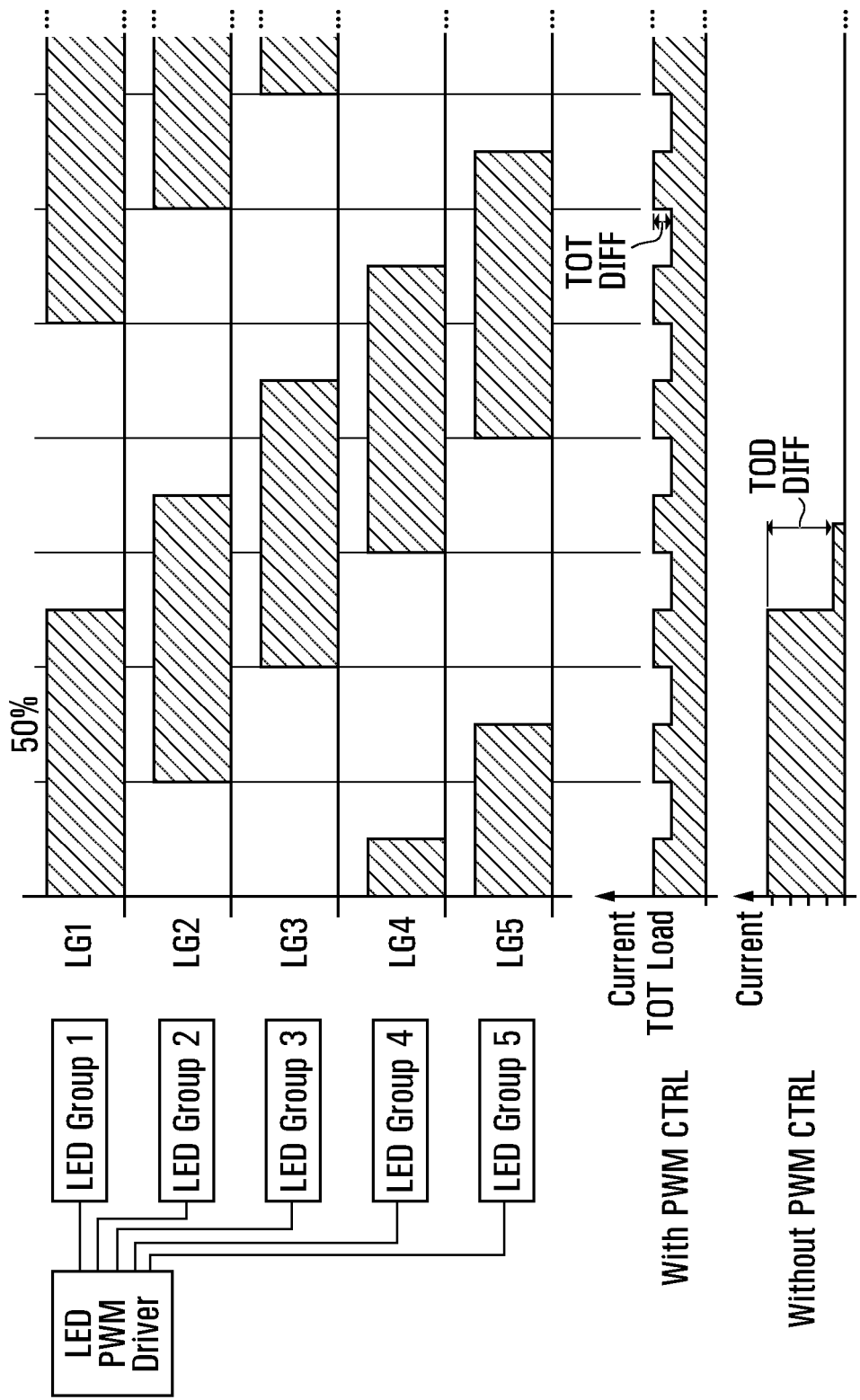
FIG. 4 shows plots of current draw over time for different groups of LEDs, according to embodiments of the disclosure.

According to some embodiments, the controller is configured to sequentially activate and deactivate one or more groups of LEDs 18, using for example pulse width modulation (PWM). As can be seen in FIG. 4, the LED array comprises groups of LEDs 18 (each group comprising one or more individual LEDs 18). Each group of LEDs 18 is asynchronously activated relative to the other groups of LEDs 18. Additionally, each group of LEDs 18 is asynchronously deactivated relative to the other groups of LEDs 18. Asynchronously activating and/or deactivating the LED groups in this fashion reduces the magnitude of current transients during activation/deactivation of the LED groups.

For example, as can be seen at the bottom of FIG. 4, the average current drawn when asynchronously activating and deactivating the LED groups is similar to the average current that is drawn when all LED groups are synchronously activated and deactivated. However, the average rate of change of current that is drawn is less when asynchronously activating and deactivating the LED groups. Reducing current transients in this fashion may reduce the effect of electromagnetic interference such as harmonic distortion.

Figure 5:
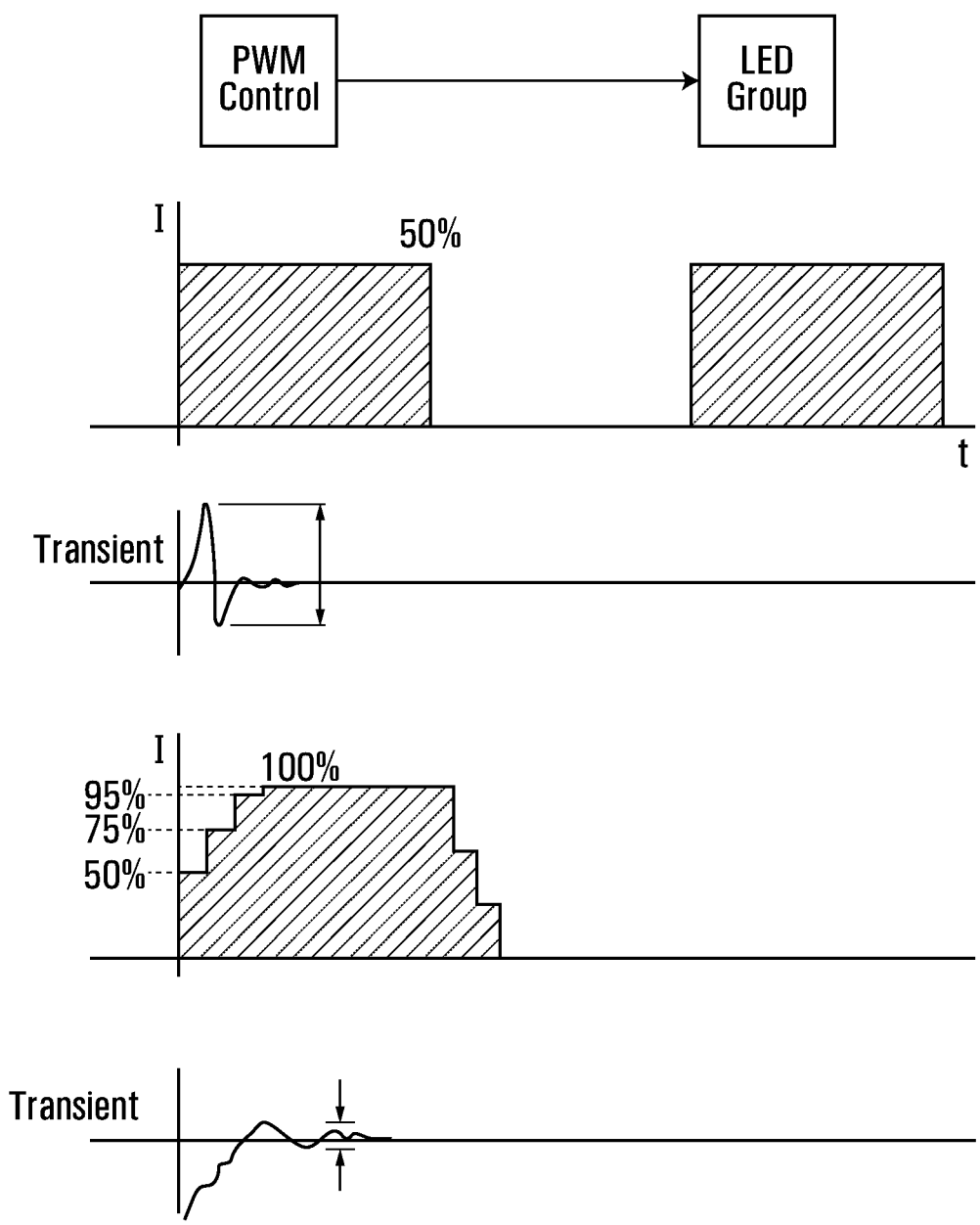
FIG. 5 shows plots of current draw over time, according to embodiments of the disclosure.

Turning to FIG. 5, there is shown another method of controlling the LED array. According to this method, the current used to drive an LED 18 is gradually adjusted. For example, an LED 18 or multiple LEDs 18 may be first driven with 50% of a total current, then 75% of the total current, then 90% of the total current, and lastly 100% of the total current. Thus, the rate of change of current is reduced, similarly to the method described in connection with FIG. 4. The method of FIG. 5 may be combined with that of FIG. 4.

The controller may be communicatively coupled to an alarm (not shown) for alerting a user when a disinfection rate of the fluid decreases below a certain threshold. The disinfection rate will depend on various factors, such as the UV transmissivity of the fluid, the power output by the LED array, and the duration the fluid is exposed to UV light within apparatus 100, which itself may be a function of the length of the fluid flow path as well as the rate of flow of the fluid through apparatus 100.

In order to determine whether the disinfection rate is too low, the controller may evaluate various factors, such as the effective power output of LEDs 18 and the rate of flow of fluid through apparatus 100. The effective power output of an LED will naturally decay through extended use, and the controller may be configured to estimate or determine this decay by measuring an intensity of UV light reflected by housing 10. For example, apparatus 100 may include one or more UV sensors communicative with the controller and configured to detect and output a reading of the intensity of UV light reflected by housing 10. In combination with the rate of fluid flow through apparatus 100, which may be determined from flow detection port 46, the controller may determine a disinfection rate of apparatus 100. The disinfection rate may be any value or parameter that relates to the effectiveness of disinfection by apparatus 100. Once the disinfection rate is determined to be too low, the controller may activate an alarm. Such an alarm may notify a user that, for example, the LEDs are in need of replacing.

Furthermore, the controller may be configured to regulate the power output of LEDs as a function of the flow rate of the fluid as detected by flow detection port 46. In particular, the output of flow detection port 46 may be read by the controller, and the controller may adjust the power output of LEDs as a function of the reading. For example, if flow detection port 46 detects a drop in the flow rate of the fluid, then the controller may correspondingly lower the power output of LEDs. Similarly, if flow detection port 46 detects an increase in the flow rate of the fluid (up to the maximum allowable as set by flow regulator 44), then the controller may correspondingly increase the power output of LEDs.

Figure 6:
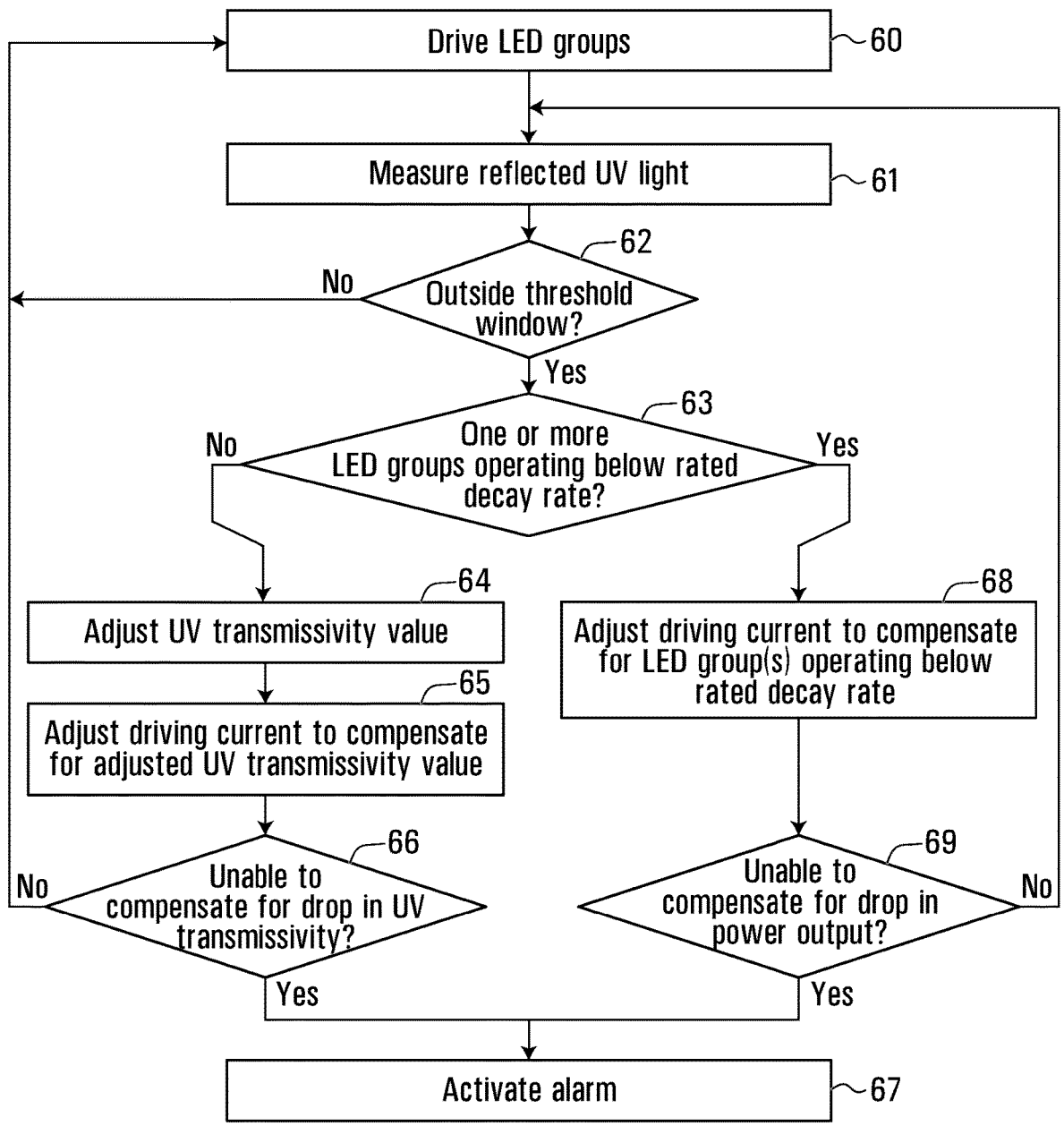
FIG. 6 is a flow diagram of a method of operating LEDs, according to embodiments of the disclosure.

The disinfection rate may also depend on the UV transmissivity of the fluid, and the controller may be further configured to adjust the power output of LEDs 18 as a function of the UV transmissivity. Turning to FIG. 6, there is shown a flow diagram of an example method that may be performed by the controller, according to embodiments of the disclosure.

At block 60, the controller drives the LEDs groups. At block 61, the controller determines an intensity of UV light that has passed through the fluid, that has been reflected from housing 10, and that has been detected by one or more UV sensors communicating with the controller. At block 62, the controller determines whether the measured intensity is outside a threshold window (e.g. a range of acceptable or expected UV intensities, for a given UV transmissivity of the fluid). If the measured intensity is within the threshold window, then the process returns to block 60. If the measured intensity is outside the threshold window, then the controller determines whether one or more of the LED groups (or one or more individual LEDs) are operating below their nominal decay rate (e.g. whether their effective power output is decaying more rapidly than expected due to extended use).

In order to do this, the controller may sequentially activate each LED group and determine, using the one or more UV sensors, whether the measured UV intensity of each LED group is within an acceptable range of UV intensities. If, for one or more of the LED groups, the measured intensity is outside the acceptable range of UV intensities, then the controller determines that those LED groups are decaying more rapidly than expected, and are contributing to the drop in measured intensity of UV light reflected by housing 10. Thus, at block 68, the controller increases a current driving the LED array in order to compensate for the faster-than-expected decay in power output of any such LED groups. At block 69, the controller determines whether, given the current UV transmissivity, it is impossible to compensate for the faster-than-expected decay in power output, for example if compensating for the faster-than-expected decay in power output would require a current driving the LED array to be increased above an upper limit. If the controller determines that it is impossible to compensate for the faster-than-expected decay in power output, then at block 67 the controller activates an alarm to warn a user. Therefore, the controller alerts the user that, given the current UV transmissivity of the fluid, and the maximum available power output of the LED array, it is not possible to sustain a minimum required disinfection rate.

Returning to block 63, if, for each LED group, the measured intensity is within the acceptable range of UV intensities, then the controller determines that the UV transmissivity of the fluid has decreased (e.g. the fluid has become more opaque to UV light). Thus, at block 64, the controller adjusts a UV transmissivity value for the fluid, and at block 65 the controller adjusts a current driving the LED array in order to compensate for the decreased UV transmissivity. At block 66, the controller determines whether it is impossible to compensate for the decreased UV transmissivity, for example if compensating for the decreased UV transmissivity would require a current driving the LED array to be increased above an upper limit. If the controller determines that it is impossible to compensate for the decreased UV transmissivity, then at block 67 the controller activates an alarm (assuming the UV transmissivity has dropped below a certain threshold). Therefore, the controller alerts the user that, given the current UV transmissivity of the fluid, and the maximum available power output of the LED array, it is not possible to sustain a minimum required disinfection rate.

According to some embodiments, LEDs 18 may be operated so as to obtain a disinfection rate of at least 16 mJ/cm$^2$ at 90% UV transmissivity, and according to some embodiments may be operated so as to obtain a disinfection rate of at least about 19 mJ/cm$^2$ at 90% UV transmissivity.

Figure 7:
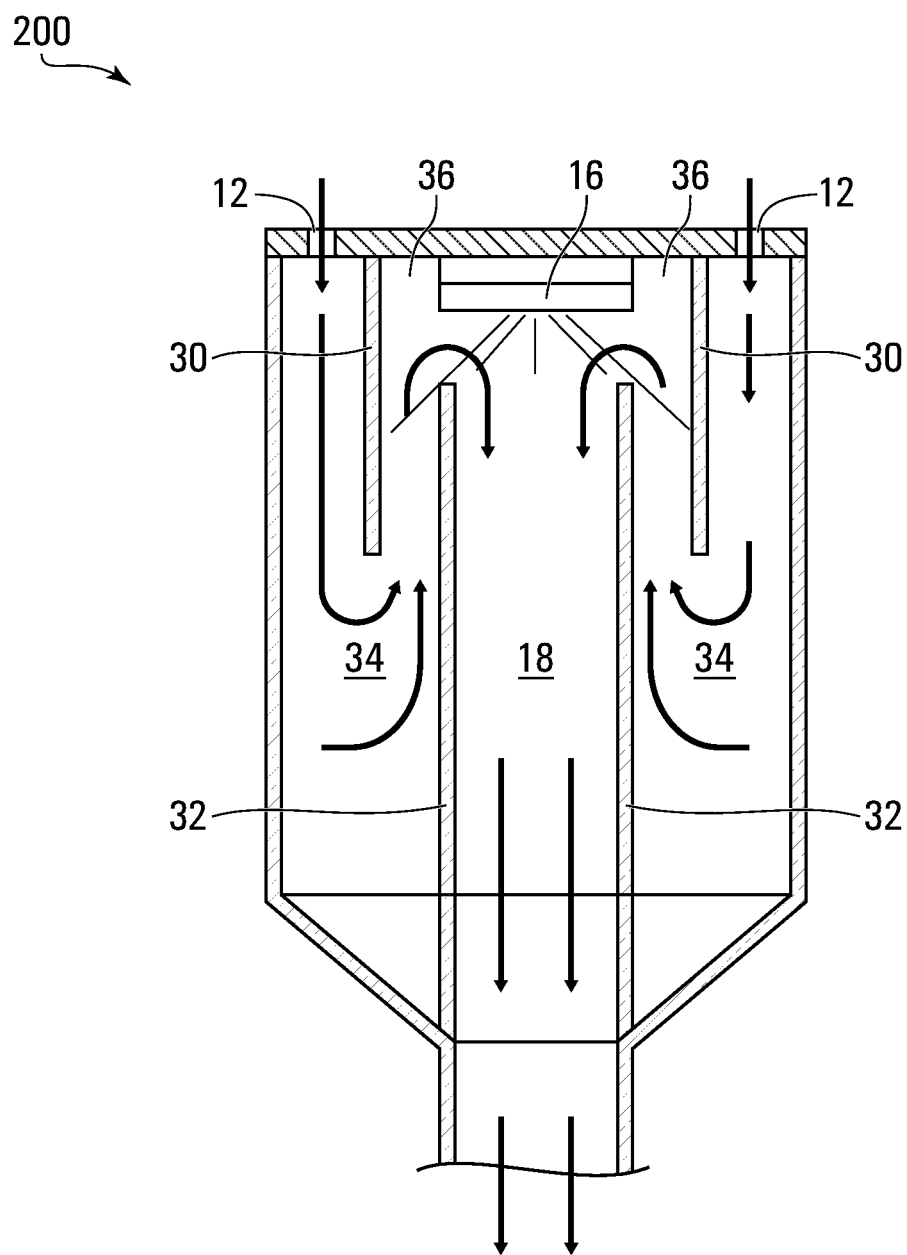
FIG. 7 is a cross-sectional view of an apparatus for disinfecting a fluid, according to embodiments of the disclosure.

Turning to FIGS. 6, 7A, and 7B, there are shown other embodiments of the disclosure, in which the baffles may be shaped differently. For example, as can be seen in FIG. 7, apparatus 200 does not include a rear chamber, but instead only uses a front chamber for cooling the LED array. In particular, fluid flowing into apparatus 200 via fluid inlet 12 is directed, by cylindrical baffles 30 and 32, along a first annular space 34 according to a first direction, subsequently along a second annular space 36 according to a second direction opposite the first direction, and then into a central chamber 38 according to the first direction. As the fluid passes from annular space 36 to chamber 38, the fluid comes into contact with LED module 16, and may absorb heat generated by the LEDs housed within LED module 16, for example by flowing into contact with an optical window provided in the front of LED module 16 (similarly to the embodiment of FIG. 1). Baffles 30 and 32 comprise an optically transparent material so that the fluid may undergo disinfection before reaching chamber 38.

Figure 8A:
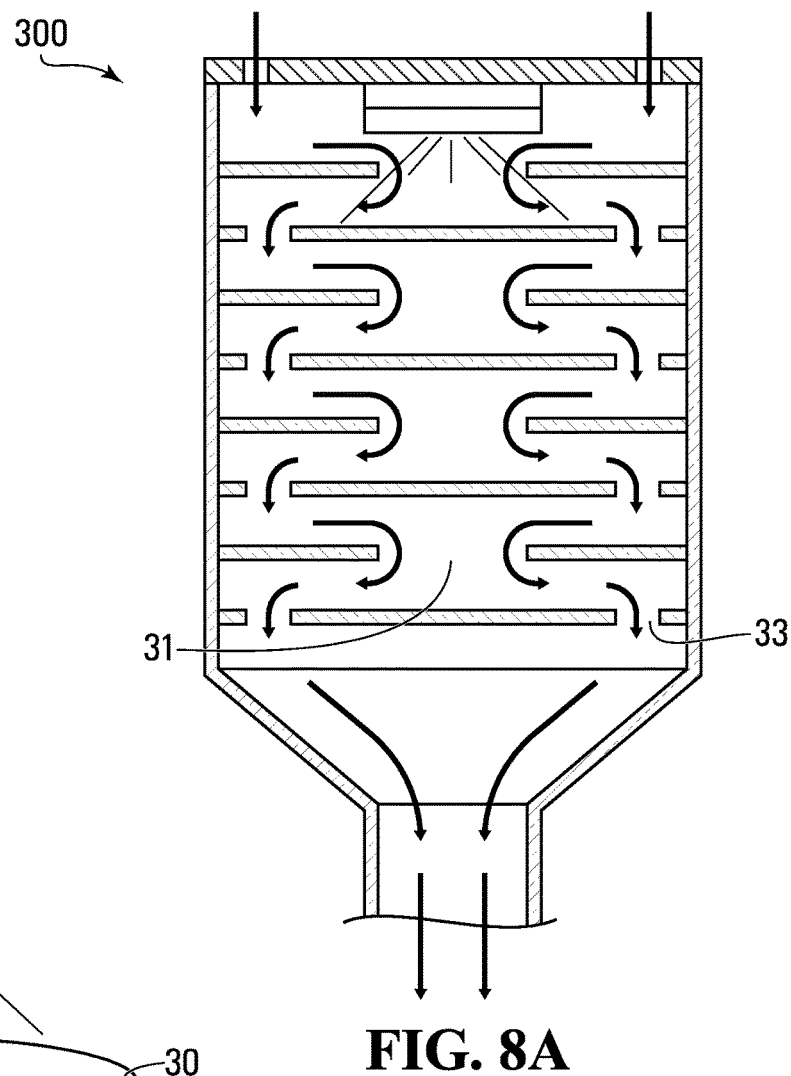
FIGS. 8A and 8B show cross-sectional and perspective views, respectively, of an apparatus for disinfecting a fluid, according to embodiments of the disclosure.
Figure 8B:
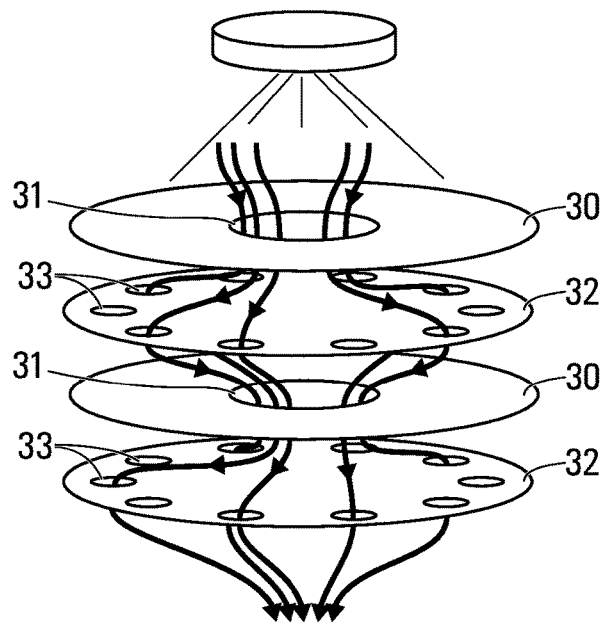

A further embodiment of an apparatus 300 for disinfecting a fluid is shown in FIGS. 8A and 8B. In this embodiment, the baffles are shaped as discs 30 and 32. The discs include annular discs 30 comprising central apertures 31 formed therein, and discs 32 with peripheral apertures 33 formed therein. Fluid flowing from the fluid inlet to the fluid outlet passes first via central aperture 31 of a first disc 30, subsequently through peripheral apertures 33 of a second disc 32, subsequently through central aperture 31 of a third disc 30, and subsequently through peripheral apertures 33 of a fourth disc 32. Thus, the fluid effects multiples passes before exiting apparatus 300.

As the skilled person will appreciate, there exists a multitude of different shapes and designs that the apparatus may embody. For example, the fluid flow path may be altered or otherwise adjusted, for instance by repositioned, omitting, or providing additional baffles. The embodiments shown and described herein represent merely some examples of how the apparatus may be designed.

Furthermore, in some embodiments, the fluid flow path may be configured such that the fluid is brought into direct contact with the PCB or other substrate on which the LEDs are mounted (for example by omitting the conductive member that separates the fluid from the PCB). In still other embodiments, the fluid flow path may be configured such that the fluid is brought into direct contact with the LEDs themselves (for example by omitting the optical window and the conductive material that separate the fluid from the LEDs).

With this in mind, while the disclosure has been described in connection with specific embodiments, it is to be understood that the disclosure is not limited to these embodiments, and that alterations, modifications, and variations of these embodiments may be carried out by the skilled person without departing from the scope of the disclosure. It is furthermore contemplated that any part of any aspect or embodiment discussed in this specification can be implemented or combined with any part of any other aspect or embodiment discussed in this specification.

The invention claimed is:

1. An apparatus for disinfecting a fluid, comprising:
    a housing comprising:
        a fluid inlet for inflow of a fluid to be disinfected; and
        a fluid outlet for outflow of the fluid to be disinfected;
    one or more light-emitting diodes (LEDs) operable to emit ultraviolet (UV) light for disinfecting the fluid to be disinfected,
    a window at least partially transparent to UV light, positioned in front of the one or more LEDs,
    wherein a fluid flow path extends from the fluid inlet to the fluid outlet and is configured such that, when the fluid to be disinfected flows along the fluid flow path, the fluid to be disinfected absorbs heat generated by the one or more LEDs,
    wherein the apparatus further comprises one or more baffles defining one or more first branches and one or more second branches of the fluid flow path, wherein the one or more first branches extend in a first direction and the one or more second branches extend in a second direction opposite the first direction,
    wherein the one or more baffles comprise one or more portions that are transparent to UV light so that the fluid to be disinfected undergoes disinfection when flowing along the one or more first branches and the one or more second branches of the fluid flow path, wherein the fluid inlet is located behind the one or more LEDs such that the fluid flow path extends from the fluid inlet to an area behind the one or more LEDs and then to the fluid outlet, and such that, when the fluid to be disinfected flows along the fluid flow path, the fluid to be disinfected flows behind the one or more LEDs and absorbs, from behind the one or more LEDs, heat generated by the one or more LEDs,
    wherein the fluid inlet comprises an opening in the housing to permit the fluid to be disinfected outside the apparatus to flow into the apparatus by passing from outside the apparatus, through the opening, and into the apparatus, and
    wherein the one or more baffles are positioned relative to the window such that the fluid to be disinfected, when flowing along the fluid flow path, flows from the area behind the one or more LEDs and away from the one or more LEDs along a branch of the one or more first branches, and then toward the one or more LEDs along a branch of the one or more second branches, before coming into contact with the window.

2. The apparatus of claim 1, wherein the one or more LEDs are mounted on one or more substrates, and wherein the one or more substrates define a boundary of at least a portion of the fluid flow path such that, when the fluid to be disinfected flows along the fluid flow path, the fluid to be disinfected flows in contact with the one or more substrates.

3. The apparatus of claim 1, wherein the one or more LEDs are mounted on one or more substrates, wherein the apparatus further comprises a conductive member on which are provided the one or more substrates, and wherein the conductive member defines a boundary of at least a portion of the fluid flow path such that, when the fluid to be disinfected flows along the fluid flow path, the fluid to be disinfected flows in contact with the conductive member.

4. The apparatus of claim 1, wherein a distance between the one or more LEDs and a portion of the fluid flow path located behind the one or more LEDs is configured such that, when the fluid to be disinfected flows along the portion of the fluid flow path, at least about 90% of heat generated by the one or more LEDs is absorbed by the fluid to be disinfected.

5. The apparatus of claim 1, wherein one or more of the following are selected such that, when the fluid to be disinfected flows along the fluid flow path, the fluid to be disinfected is disinfected at a rate of at least about 16 mJ/cm$^2$ at 90% UV transmissivity of the fluid:
- a length of the fluid flow path;
- a setting of a flow regulator for controlling a rate of flow of the fluid to be disinfected; and
- a power output of the one or more LEDs.

6. The apparatus of claim 1, wherein the one or more baffles further define one or more annular spaces within the housing.

7. The apparatus of claim 6, wherein the one or more baffles are configured such that, when the fluid to be disinfected flows along the fluid flow path, the fluid to be disinfected flows from a near end to an opposite far end of a first one of the one or more annular spaces, and then from a far end to an opposite near end of a second one of the one or more annular spaces.

8. The apparatus of claim 6, wherein the one or more annular spaces comprise a sequence of annular spaces, and wherein the one or more baffles are configured such that, when the fluid to be disinfected flows along the fluid flow path, the fluid to be disinfected flows sequentially from one annular space to the next annular space in the sequence of annular spaces.

9. The apparatus of claim 1, wherein the one or more baffles are configured such that a direction of the fluid flow path is reversed at least once.

10. The apparatus of claim 1, wherein the one or more LEDs define one or more light beams, and wherein:
- one or more first portions of the fluid flow path do not pass through the one or more light beams; and/or
- one or more second portions of the fluid flow path pass through the one or more light beams.

11. The apparatus of claim 1, wherein one or more portions of the fluid flow path pass in front of the one or more LEDs such that, when the fluid to be disinfected flows along the one or more portions of the fluid flow path, the fluid to be disinfected absorbs, from in front of the one or more LEDs, heat generated by the one or more LEDs.

12. The apparatus of claim 1, further comprising:
- a conductive material positioned between the one or more LEDs and the window.

13. The apparatus of claim 12, wherein the conductive material comprises a thermally conductive foam.

14. The apparatus of claim 12, wherein the conductive material is in contact with the one or more LEDs and the window.

15. The apparatus of claim 12, wherein the window defines a boundary of at least a portion of the fluid flow path such that, when the fluid to be disinfected flows along the fluid flow path, the fluid to be disinfected flows in contact with the window.

16. The apparatus of claim 1, wherein the fluid inlet is off-axis relative to the one or more LEDs.

17. The apparatus of claim 1, wherein the housing comprises a reflective surface for reflecting UV light.

18. The apparatus of claim 1, wherein the apparatus further comprises a controller configured to control the one or more LEDs.

19. The apparatus of claim 18, wherein the controller is further configured to activate an alarm in response to determining that a disinfection rate, or a UV transmissivity of the fluid, has dropped below a preset threshold.

20. The apparatus of claim 18, wherein the controller is further configured to:
- determine an intensity of UV light having passed through a fluid flowing through the apparatus;
- determine whether the measured intensity is outside a threshold window; and
- if the measured intensity is outside the threshold window, adjust a current driving the one or more LEDs.

21. The apparatus of claim 20, wherein the one or more LEDs comprise multiple groups of LEDs, each group of LEDs comprising one or more LEDs, and wherein the controller is further configured to, after determining that the measured intensity is outside the threshold window and before adjusting the current:
- sequentially drive each group of LEDs; and
- for each group of LEDs, determine whether a power output of at least one of the LEDs in the group of LEDs is less than an expected power output; and
- if the power output of the at least one of the LEDs is less than the expected power output, then the adjusting of the current driving the one or more LEDs is based on the power output of the at least one of the LEDs, to compensate for the power output of the at least one of the LEDs; and
- if the power output of the at least one of the LEDs is not less than the expected power output, then the controller is further configured to adjust a UV transmissivity value of the fluid, and wherein the adjusting of the current driving the one or more LEDs is based on the adjusted UV transmissivity value, to compensate for the adjusted UV transmissivity value.

22. The apparatus of claim 21, wherein determining whether the power output of the at least one of the LEDs is less than an expected power output comprises:
- determining with the controller an intensity of UV light having passed through a fluid flowing through the apparatus; and
- determining with the controller whether the measured intensity of UV light is below an expected threshold.

23. The apparatus of claim 1, further comprising one or more sensors for detecting an intensity of UV light reflected from the housing.

24. The apparatus of claim 1, further comprising a flow sensor for detecting a flow rate of the fluid to be disinfected through the apparatus.

25. The apparatus of claim 1, wherein the apparatus does not comprise any additional means for cooling the one or more LEDs.

26. The apparatus of claim 25, wherein the additional means comprise a separate fluid inlet and a separate fluid outlet for receiving a separate coolant for cooling the one or more LEDs.

27. The apparatus of claim 25, wherein the additional means comprise a heatsink.

28. The apparatus of claim 1, wherein the one or more baffles define a pair of annular spaces, wherein the branch of the one or more first branches is fluidly connected to the branch of the one or more second branches at ends of the annular spaces that are furthest from the one or more LEDs, and wherein the fluid to be disinfected, when flowing along the fluid flow path, reverses its direction of flow at the ends of the annular spaces that are furthest from the one or more LEDs.

* * * * *